Figure 1:
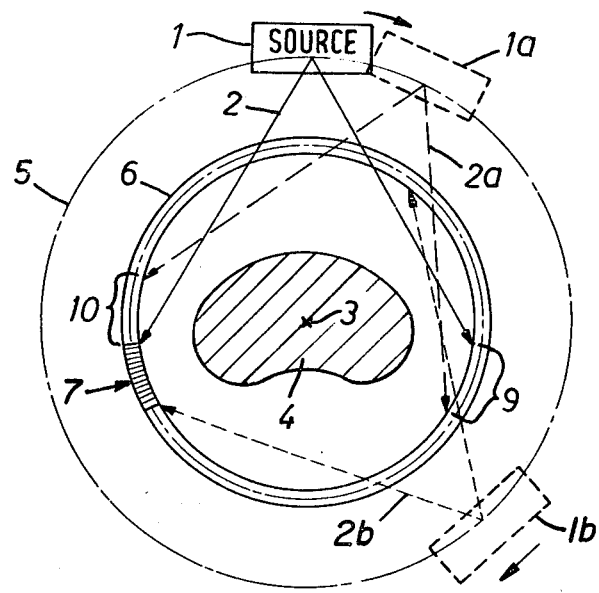

United States Patent [19]

Fetter

[11] 4,137,455
[45] Jan. 30, 1979

[54] MEDICAL RADIOGRAPHIC APPARATUS WITH MEANS FOR NOTATING DETECTOR RING

[75] Inventor: Richard W. Fetter, Warrenville, Ill.

[73] Assignee: EMI Limited, Middlesex, United Kingdom

[21] Appl. No.: 811,279

[22] Filed: Jun. 29, 1977

[51] Int. Cl.² .............................................. A61B 6/02
[52] U.S. Cl. ................................. 250/445 T; 250/360
[58] Field of Search ........................... 250/445 T, 360

[56] References Cited
U.S. PATENT DOCUMENTS

| 4,005,311 | 1/1977 | Ledley | 250/445 T |
| 4,031,395 | 6/1977 | LeMay | 250/360 |
| 4,045,672 | 8/1977 | Watanabe | 250/445 T |

Primary Examiner—Alfred E. Smith
Assistant Examiner—T. N. Grigsby
Attorney, Agent, or Firm—Cooper, Dunham, Clark, Griffin & Moran

[57] ABSTRACT

In a computer-assisted tomography (CAT) apparatus, in which a fan-shaped X-ray distribution is rotated about the patients body, it is possible to use a ring of stationary detectors disposed to receive the radiation after passage through the body. In this arrangement the ring of detectors is of smaller radius than the locus of motion of the radiation source. It would appear that this would cause the detectors to obscure the body from the radiation. An arrangement disclosed moves out of the radiation beam those detectors which would present an obstruction so that only those required to collect radiation lie in the beam.

11 Claims, 10 Drawing Figures

MEDICAL RADIOGRAPHIC APPARATUS WITH MEANS FOR NOTATING DETECTOR RING

The present invention relates to medical radiographic apparatus, and it relates more particularly to such apparatus, commonly known as computer-assisted tomographic apparatus, for obtaining representations of the variation of absorption of penetrating radiation over cross-sectional slices of the bodies of human patients.

Computer-assisted tomography (C.A.T.) was invented by Godfrey Newbold Hounsfield, and a number of examples of apparatus for performing C.A.T. are described in his U.S. Pat. No. 3,778,614. Inspection of that U.S. patent will indicate that Hounsfield had realised that rapid patient scanning could be effected by rotating a source of a substantially planar, fan-shaped distribution of X-rays around a patient and providing a number of radiation-sensitive detectors which could simultaneously detect radiation transmitted through the patient's body along a number of beams within the distribution.

As C.A.T. has become established, the cost of detectors and their associated circuitry has fallen, making it feasible to construct C.A.T. apparatus employing a full, circular array of detectors which surrounds the patient's body and within which a source of a fan-shaped distribution of X-rays, as taught by Hounsfield, rotates. However, the cost of the detector and associated circuitry is still considerable, and it is an object of this invention to reduce the expenditure on such components in a medical radiographic apparatus. The inventor has realised that the number, and thus the cost, of detectors can be reduced by putting the ring of detectors between the X-ray source and the patient's body. This is a rather unexpected step to take, because it presents a problem in that the detectors for the time being disposed at the same side of the body as the X-ray source would, if no steps were taken to the contrary, interrupt the radiation so that the radiation would not pass through the patient's body to be collected by the detectors for the time being disposed at the opposite side of the body to the source. It is another object of this invention to overcome that problem.

The invention provides medical radiographic apparatus, for investigating a cross-sectional slice of a patient's body, including a source of a fan-shaped distribution of penetrating radiation, such as X-radiation, locating means for locating the source, in relation to the patient's body, so that said radiation is directed towards said slice, scanning means for rotating said source around the patient's body to direct radiation towards said slice from a plurality of different directions, detector means comprising a plurality of detector devices, sensitive to said radiation, disposed along an arcuate path surrounding, or partly surrounding, the patient's body, the detector devices being substantially immobile in the direction of rotation of said source, means locating said detector devices such that said arcuate path is closer to the patient's body than the source of radiation throughout the rotational movement of said source, and means for moving detector devices for the time being disposed at the same side of the patient's body as the source so that they do not interrupt the detection of said radiation by detector devices for the time being disposed at the opposite side of the patient's body to said source.

Figure 2:
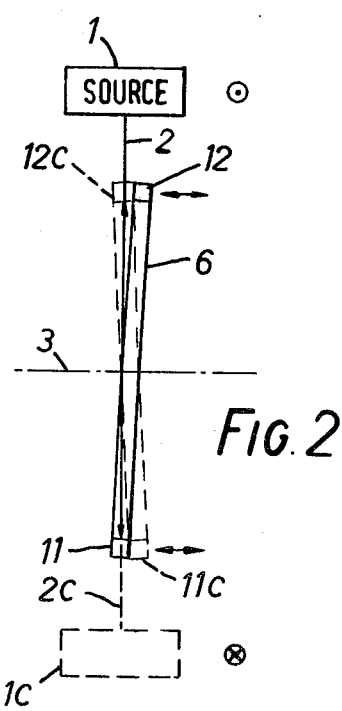
Figure 3:
Figure 4:
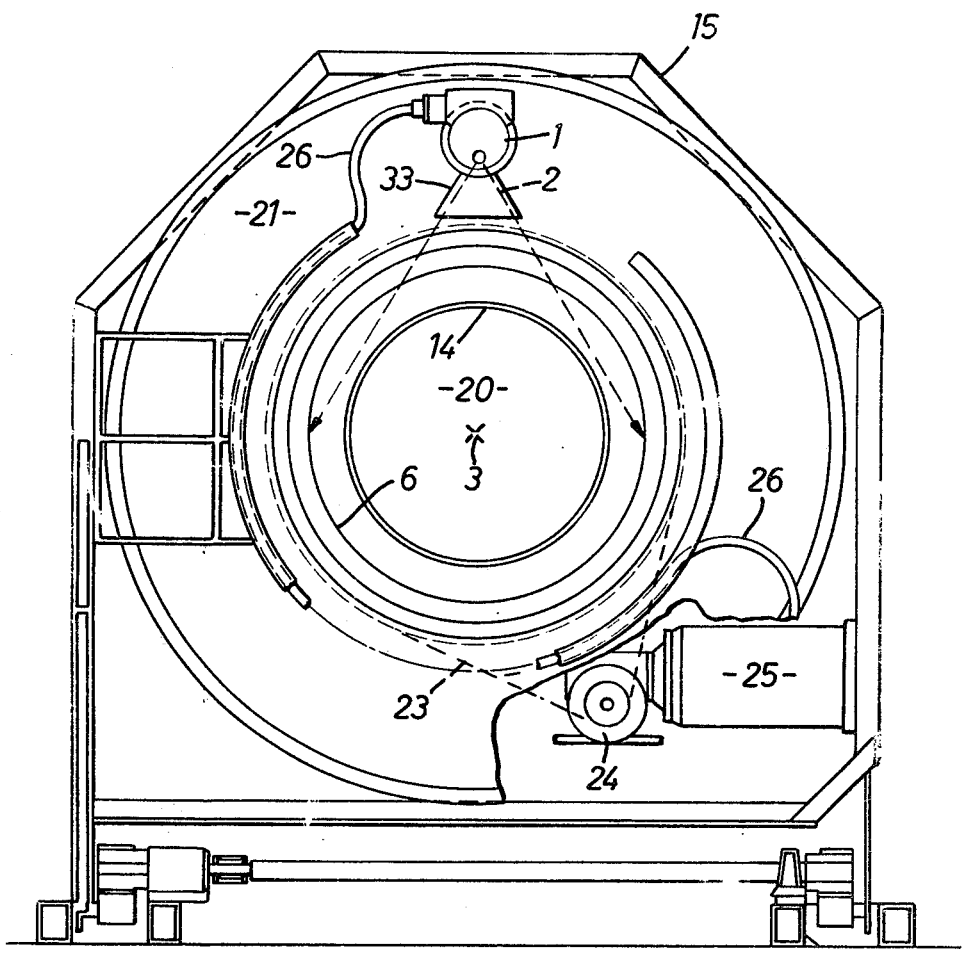
Figure 5:
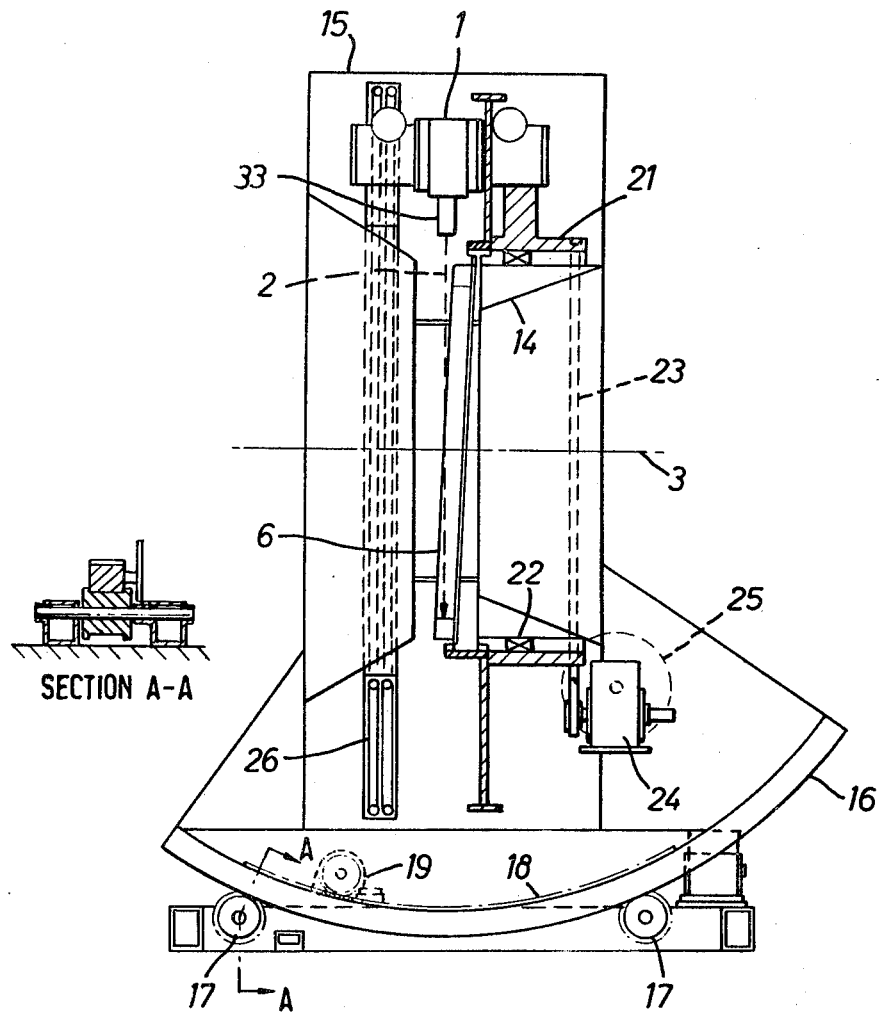
Figure 6:
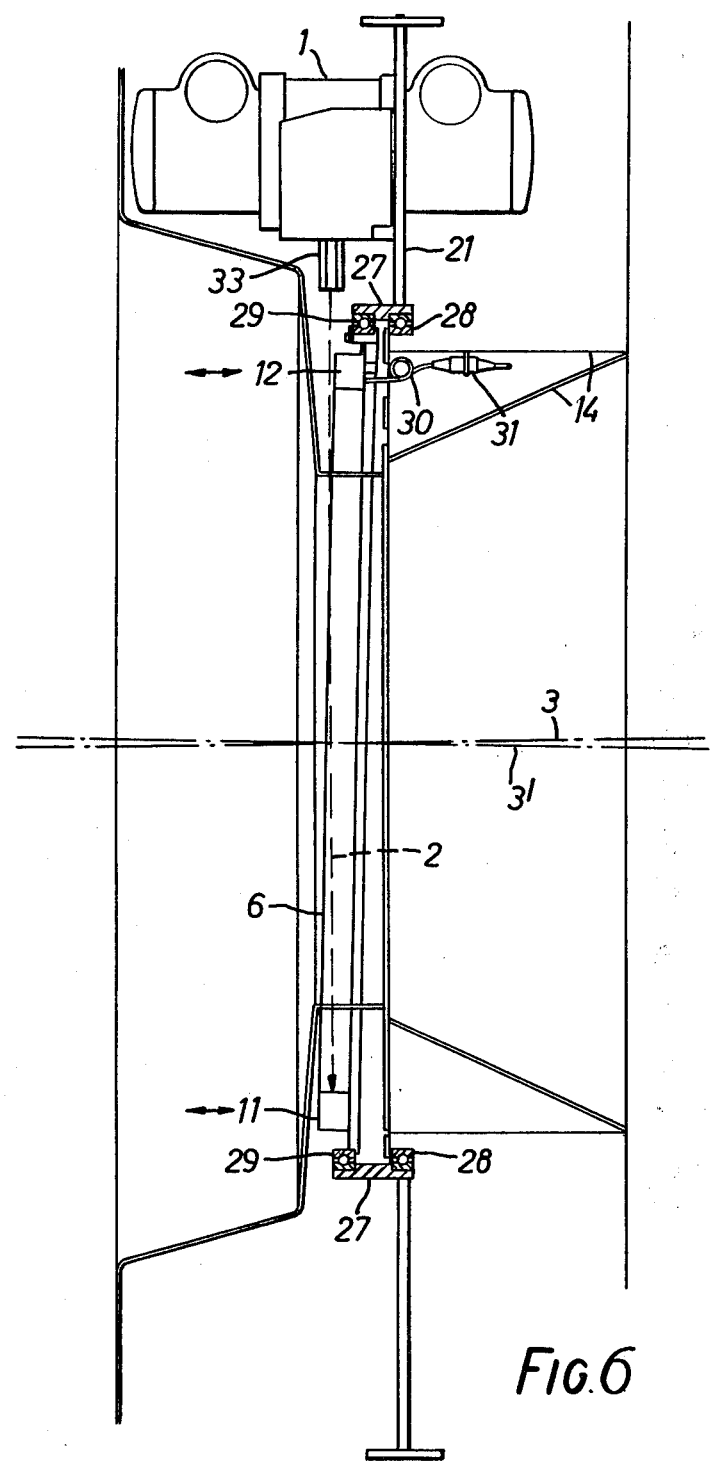
Figure 7:
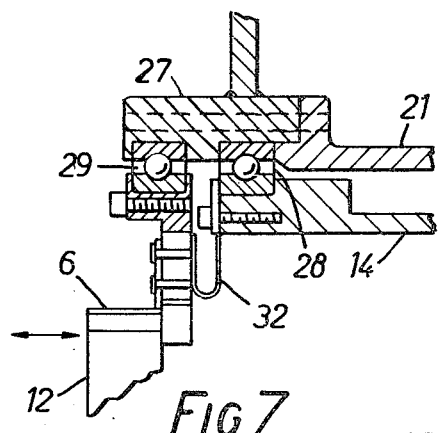
Figure 8:
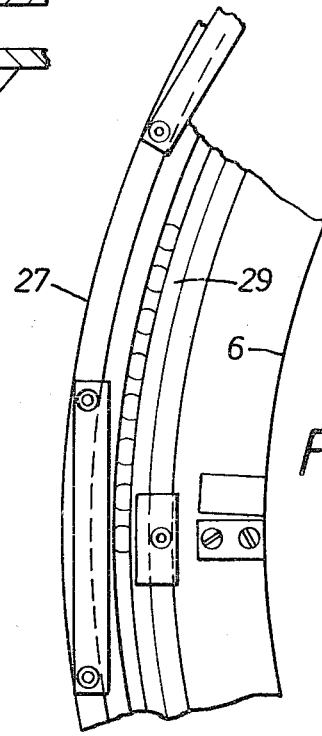
Figure 10:
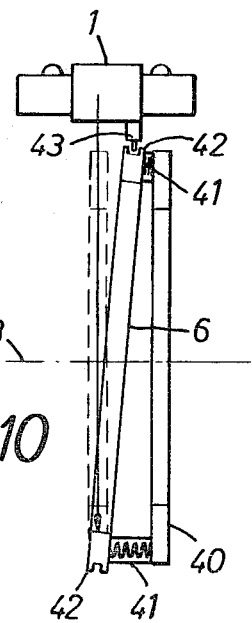
Figure 9:
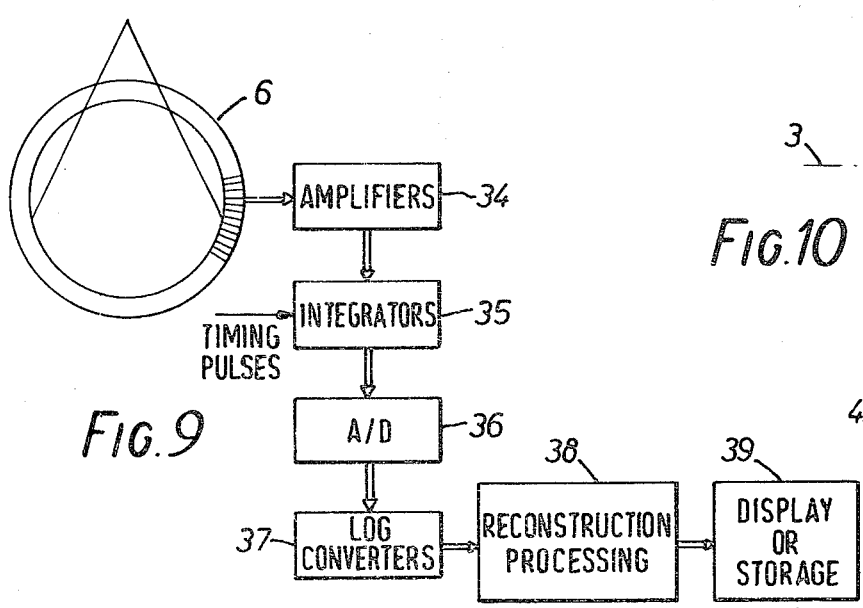

In order that the invention may be clearly understood and readily carried into effect examples thereof will now be described with reference to the accompanying drawings of which FIGS. 1 and 2 illustrate a simplified apparatus, incorporating the invention, in front and side elevation respectively, FIG. 3 is used to explain the manner in which radiation intercepts the detectors, FIGS. 4 and 5 illustrate a practical embodiment of the invention in front and side elevation respectively, FIG. 6 shows the arrangement used to mount the detectors, FIGS. 7 and 8 show details of the detector guiding arrangement, FIG. 9 shows a simplified circuit for processing data derived from an apparatus according to the invention and FIG. 10 shows an alternative arrangement for providing the nutating motion.

There is shown in schematic form in FIG. 1 a scanning arrangement which is an alternative to the fixed detector systems discussed hereinbefore. This arrangement performs a different scanning motion but provides absorption data in a form similar to that of the fixed detector systems so that the processing can be substantially similar to that which may be used with those systems.

The apparatus includes an X-ray tube 1 which is a source of a fan-shaped distribution 2 of X-rays. The fan-shaped distribution is, in this example, substantially co-planar with the plane of the Figure. Tube 1 is orbited about an axis 3, perpendicular to said plane, which intersects an aperture in which the body 4 of a patient may be situated for examination. The locus of rotation of the point of origin of the X-rays is shown by the chain dotted circle 5.

Disposed at a constant radius from axis 3 there is a ring 6 of detector devices of which a few are indicated at 7. These detectors may be scintillator crystals cooperating with photomultipliers or, as in this example, with photodiodes.

Although in this example the detectors extend over a complete 360° ring, it is not necessary that this be so. It is, however, desirable that they extend over at least 180°.

The X-ray fan 2 shown in FIG. 1 is of 60° extent and irradiates slightly less than half of the total number of detectors. In the course of rotation the fan 2 irradiates progressively different detectors so that for a source at 1a the fan 2a of radiation irradiates detectors over the span between the long dashed arrows. Thus between 1 and 1a the radiation leaves detector 9 and irradiates instead detectors 10.

In this example irradiation continues over a full 360° of rotation of source 1. At a subsequent source position 1b the fan 2b of radiation irradiates detectors between the short dashed arrows. Clearly some of these detectors would intercept the radiation of earlier source positions, such as 1a, if the detector ring and locus 5 were coplanar. It is to avoid this problem that other arrangements situate the source locus inside the radius of the detector ring 6.

The present invention places the source locus outside that ring, thus reducing the extent of detector ring and associated collimators required. However it ensures that any detectors which would otherwise pass between the source and the patient's body are displaced so as to allow the radiation 2 to pass unobstructed. Many different arrangements can be adopted to ensure that the detectors only intercept the radiation as required. The preferred arrangement of this example uses a detector ring which does not have any angular motion relative to the body about axis 3 but which is subject to a nutation to obtain the desired relationship.

It should be noted that not only does the possible reduced size of the detector ring and collimators allow reduced size and complexity for those and other parts of the apparatus, for example the scanning gantry, but also it allows more efficient use of the x-ray photons and consequent reduced power and cooling requirements for the X-ray tube. This latter improvement results from a reduced source to image distance between source and detectors obtained by putting the detector ring at smaller radius than a source which is substantially as close to the patient as is normally acceptable.

The arrangement can be more clearly seen from FIG. 2 which is a side elevation of FIG. 1. At position 1 the source, which is moving out of the page as shown by the arrow head, projects the radiation along 2 to intercept the body, not shown, and, for a beam in the plane of the paper, a detector 11. The 180° opposing detector 12 is displaced to the right to allow the radiation to pass. As the source is orbited, the detector ring is subjected to the nutating motion indicated by the horizontal arrows. This ensures that, when the source is at the 180° opposing position 1c, the radiation at 2c, still in the same plane, intercepts detector 12 at 12c but is not obstructed by detector 11 at 11c.

Clearly the nutating motion and offset position of the detector ring 6 means that the detectors lie on an apparently curved path as viewed from the source 1. To avoid problems from this the detectors should be of sufficient width to intercept the entire thickness of the fan of radiation over its entire extent.

FIG. 3 shows the effect of this, as viewed from the source at 1a. In this Figure the line of incidence of the radiation is shown at 13. It can be seen that the radiation is fully intercepted by detectors across the entire fan, including the newly irradiated detectors 10. However detectors 9, which would not fully intercept the fan, are not irradiated. This arrangement does mean that the region of the detector which is irradiated varies between the center and opposite edges. For this reason it is preferable to use detectors which have a uniform response over the entire receiving surface or to predetermine corrections for differences in sensitivity.

FIG. 1 also shows that the radiation is of sufficient extent for some detectors to receive radiation which has not passed through the patient's body 4. This means that, in the course of the orbit, all of the detectors will receive some radiation which has not passed through body 4 and which, therefore, provides a calibration signal for correcting differences between detector sensitivities. It will also be apparent that irradiation need not be confined to one source provided the detector arrangement does not allow any detectors to block the radiation between a source and the body 4.

The practical arrangement for implementing this example of the invention is shown in FIGS. 4 and 5, which respectively show front and side elevations of the entire apparatus, and subsequent FIGS. 6 – 8. FIGS. 4 – 8 show the basic equipment required to implement the invention but omit many details familiar to CAT machines and which will be well known to those skilled in the art.

The apparatus includes a main frame 14 together with an outer cover 15. These may be mounted directly on the floor but in the example shown are mounted on a rocker 16 which cooperates with rollers 17 and is driven, via gear teeth 18, by motor 19 to provide a tilting facility of axis 3.

Frame 14 and cover 15 have an aperture 20, to which axis 3 is central, to admit the patient, not shown.

The X-ray tube 1 is supported on a member 21 which is rotatable about axis 3 on bearings 22. The member 21 is driven, via a belt 23 and gearbox 24, by a motor 25 mounted on the main frame. Power supplies and cooling oil to the X-ray tube 1 are carried by cables 26, which are of sufficient extent and have a suitable cabling handling arrangement to allow the tube to revolve through a working 360° plus, say, 180° to come to working angular velocity and, say, 180° to stop.

The detector ring 6 is mounted to encircle aperture 20, in a fixed angular relation with main frame 14 but capable of the nutation described hereinbefore. This arrangement can be seen in more detail in FIG. 6, which shows only the relevant features.

As can be seen from FIG. 6, member 21, which is not shown in full, includes a ring 27 having two bearings, in the form of ball bearings 28 and 29. Bearing 28 is disposed parallel to the plane of the radiation and is an additional bearing between member 21 and main frame 14. Bearing 29 is, however, inclined to that plane, to bring its axis to 3', and supports the detector ring 6.

The position of bearing 28 is determined by fixed member 14 and the relative positions of bearings 28 and 29 is determined by their relative positions, as shown, on ring 27. Thus in operation, as ring 27 is rotated with member 21, bearings 29 cause the ring 6 and individual detectors, such as 11 and 12, to execute the nutating motions shown.

Each detector is connected by a looped wire 30 to a terminal 31 mounted on main frame 14. From the terminals 31, cables supply the detector outputs to processing circuits not shown.

It will be apparent that the rotation of member 21 and ring 27 will tend to cause detector ring 6 to rotate although it would be restrained by the wires 30. It is not, however desired that ring 6 has any rotational motion and for this reason it is also connected to main frame 14 by a series of anti-rotation webs 32 which are not flexible in the direction of rotation but are flexible perpendicular to that direction. The anti-rotation webs, one of which can be seen in the detail drawing of FIG. 7, allow the desired nutating motion of ring 6 but prevent rotation. Suitable material for these webs is spring steel strip.

Further details of the ball bearing 29 can be seen in FIG. 8.

Bearing 29 positions ring 6 so that the detectors fully intercept the planar fan 2, of radiation, over the full extent, as shown in FIGS. 1 and 2, but do not obscure the radiation prior to the patient's body. To ensure that the radiation is sufficiently confined to a plane to allow this, a fan shaped collimator 33 is provided at the tube 1. Further collimators, not shown, may be provided at the detectors to exclude radiation scattered in the patient's body. These collimators must however, admit radiation over the full range of the source motion for which a detector is irradiated. This may be arranged by having collimators moving with the source 1.

It is desirable to monitor the progress of the source scan so as to properly organise the data provided by the detectors. This may be provided by a transparent ring carrying graticule markings, mounted on member 21, and a stationary light source and photocell detecting passage of the markings. However the progressive irradiation of different detectors by the advancing radiation indicates scan progress directly.

As mentioned hereinbefore the data provided by the detectors may be processed in known manner to provide the desired representation of absorption of the radiation. This may be as described in U.S. Pat. No. 3,778,614 or by the convolution process described and claimed in U.S. Pat. No. 3,924,129. The processing is indicated in FIG. 9. The data from the detectors are taken as they are derived to amplifiers 34. An individual amplifier is, in principle, required for each detector. However in practice, because the detectors are not all irradiated at the same time, some multiplexing of outputs is possible, with consequent saving of equipment. The data signals are then integrated in integrators for a period which represents one beam of radiation as received by that detector, taking into account the source motion in that time. The required timing signals are provided by the source position indicators as described hereinbefore. The data signals are then subject to analogue to digital conversion in converters 36 and are converted into logarithmic form in converters 37 to provide signals suitable for reconstruction processing in circuits 38.

As mentioned hereinbefore circuits 38 may process the data as described in U.S. Pat. No. 3,778,614 or as described in U.S. Pat. No. 3,924,129. In the latter case the convolution processing may be of a form requiring data for sets of parallel beams of radiation in which case the data must be presorted into the correct sequence.

Alternatively the convolution processing used may be appropriate to data for sets of beams in a fan-shaped distribution so that no presorting is needed. Of course any other processing suitable for CAT equipment may be used as desired.

The processed data are finally diplayed on suitable equipment such as a T.V. monitor or line printer or stored for future use, on equipment indicated generally at 39.

It has been mentioned that other arrangements may be adopted to provide the desired detector motion. For example the detector ring may be mounted on a fixed ring by a series of resilient members. These members can be arranged so that they urge the detector ring into the plane of the radiation but so that any part of the detector ring can be pushed out of the radiation by deforming the resilient members. The source can then be provided with a cam arrangement so that, as it progresses, it pushes out of the radiation that part of the detector ring having detectors which would obscure the body. The resilient members will tend to restore to position that part of the ring opposing the source.

FIG. 10 shows in simplified form an arrangement in which the detector ring 6 is mounted on a fixed ring 40 by resilient members, some of which are shown at 41, in the form of springs in flexible cases to limit outward travel. The springs are arranged to be still in compression when their expansion is so limited; at which point the detectors lie in the path of the radiation.

The detector ring 6 is formed with a peripheral cam ring 42 which engages with a cam follower 43 fixed to X-ray tube 1. As tube 1 rotates about axis 3 the cam follower 43 engages ring 42 and forces the ring 6 out of the X-ray beam against the action of local springs 41.

Other alternative arrangements falling within the scope of the invention may readily be devised.

What I claim is:

1. Medical radiographic apparatus, for investigating a cross-sectional slice of a patient's body, including a source of a fan-shaped distribution of penetrating radiation, such as X-radiation, locating means for locating the source, in relation to the patient's body, so that said radiation is directed towards said slice, scanning means for rotating said source around the patient's body to direct radiation towards said slice from a plurality of different directions, detector means comprising a plurality of detector devices, sensitive to said radiation, disposed along an arcuate path surrounding, or partly surrounding, the patient's body, the detector devices being substantially immobile in the direction of rotation of said source, means locating said detector devices such that said arcuate path is closer to the patient's body than the source of radiation throughout the rotational movement of said source, and means for moving detector devices for the time being disposed at the same side of the patient's body as the source so that they do not interrupt the detection of said radiation by detector devices for the time being disposed at the opposite side of the patient's body to said source.

2. Apparatus according to claim 1 including a ring member, on which the detector devices are mounted to intercept the radiation after passage through the patient's body, and in which the means for moving is arranged to move said ring member.

3. Apparatus according to claim 2 including a further ring member, disposed with its axis coincident with the axis of rotation of the source of radiation linked to the source to rotate therewith and in which the means for moving comprise a guiding means mounted thereon to maintain the axis of the first mentioned ring member with its axis inclined to the axis of rotation.

4. Apparatus according to claim 2 including resilient means disposed to urge the ring member into the path of the radiation and in which the means for moving comprise a cam member, linked to the radiation source, arranged to deflect the ring member against said resilient means.

5. Apparatus according to claim 4 in which the resilient means comprise a plurality of spring means.

6. Apparatus according to claim 1 in which the detector devices are distributed over 360° about the patient's body.

7. Apparatus according to claim 1 including a plurality of anti-rotation means, which are resilient in a direction perpendicular to the plane of the detector ring but not resilient in a direction tangential thereto, connecting the detector ring with stationary parts of the apparatus to maintain the detectors substantially immobile in said direction of rotation.

8. Apparatus according to claim 7 in which the anti-rotation means comprise flexible metal strips.

9. Medical radiographic apparatus for investigating a cross-sectional slice of a patient's body, the apparatus including: a source of a fan-shaped distribution of X-radiation; locating means for locating the source, in relation to the patient's body, so that said radiation is directed towards said slice; scanning means for orbiting the source about the patient's body so as to direct radiation towards said slice from a plurality of different directions; detector means comprising a ring member, of radius less than the radius of the orbit of the source, and a plurality of detector devices, sensitive to the radiation thereby, mounted thereon to intercept the radiation after passage through the slice; deflecting means, linked to the source, arranged to deflect the ring member during the orbit of the source to prevent interception of the radiation prior to passage through the slice; and means arranged to prevent motion of said ring member in the direction of orbit of the source.

10. Medical radiographic apparatus for investigating a cross-sectional slice of a patient's body, the apparatus including: a source of a substantially planar fan-shaped distribution of penetrating radiation locating means for locating the source, in relation to the patient's body, so that radiation is directed towards said slice; scanning means for orbiting the source about an axis perpendicular to the slice so as to direct radiation towards the slice from a plurality of directions; detector means comprising a plurality of detector devices disposed around the patient's body in a ring, of radius less than the orbital radius of the source, about an axis inclined to the orbital axis of the source; deflecting means, linked to the source, for nutating the axis of the detector ring about said orbital axis to cause the detectors to intercept the radiation only after it has passed through the body; and means for preventing rotation of the detectors about the nutating axis.

11. A medical diagnostic X-ray machine for producing an X-ray picture of the anatomy of a slice which extends along a planar section through the patient including:
   means for producing a fan-shaped distribution of X-radiation directed at the patient and passing through the entire slice from an origin moving along a source orbit which surrounds and is coplanar with the slice;
   detectors of X-radiation which face the slice and are arranged in a ring which surrounds the slice and is within the source orbit; and
   means for nutating the detector ring in synchronism with the motion of the origin along the source orbit to prevent interception of the X-radiation from the origin by detectors which are between the origin and the slice, but to cause interception of the X-radiation from the origin by detectors facing the side of the slice which is away from the origin.

* * * * *

UNITED STATES PATENT AND TRADEMARK OFFICE
CERTIFICATE OF CORRECTION

PATENT NO. : 4,137,455
DATED : January 30, 1979
INVENTOR(S) : RICHARD W. FETTER

It is certified that error appears in the above-identified patent and that said Letters Patent are hereby corrected as shown below:

In the TITLE, delete "NOTATING" and insert -- NUTATING --.

Column 7, line 9 (Claim 10), after "radiation" and before "locating" insert -- ; -- (semi-colon).

Signed and Sealed this

Twenty-fourth Day of June 1980

[SEAL]

Attest:

SIDNEY A. DIAMOND

Attesting Officer

Commissioner of Patents and Trademarks